(12) United States Patent
Burja et al.

(10) Patent No.: US 11,814,665 B2
(45) Date of Patent: Nov. 14, 2023

(54) ENHANCED PRODUCTION OF LIPIDS BY LIMITATION OF AT LEAST TWO LIMITING NUTRIENT SOURCES

(71) Applicants: EVONIK OPERATIONS GMBH, Essen (DE); DSM IP ASSETS B.V., TE Heerlen (NL)

(72) Inventors: Adam Burja, Potomac, MD (US); James Corona, Lutherville, MD (US); Jose R. Garcia, Lorton, VA (US); Goncalo Oliveira Maia, Columbia, MD (US); Horst Priefert, Ostbevern (DE); Joachim Windau, Warendorf (DE); Gabriel Závodský, Banska Bystrica (SK)

(73) Assignees: Evonik Operations GmbH, Essen (DE); DSM IP Assets B.V., Te Heerlen (NL)

( * ) Notice: Subject to any disclaimer, the term of this patent is extended or adjusted under 35 U.S.C. 154(b) by 382 days.

(21) Appl. No.: 16/639,529

(22) PCT Filed: Jul. 18, 2018

(86) PCT No.: PCT/EP2018/069454
§ 371 (c)(1),
(2) Date: Feb. 14, 2020

(87) PCT Pub. No.: WO2019/034354
PCT Pub. Date: Feb. 21, 2019

(65) Prior Publication Data
US 2021/0171991 A1 Jun. 10, 2021

Related U.S. Application Data

(60) Provisional application No. 62/546,808, filed on Aug. 17, 2017.

(30) Foreign Application Priority Data

Sep. 21, 2017 (EP) .................................... 17192347

(51) Int. Cl.
*C12P 7/6472* (2022.01)
*C11B 1/02* (2006.01)
*C12N 1/38* (2006.01)

(52) U.S. Cl.
CPC ............ *C12P 7/6472* (2013.01); *C11B 1/025* (2013.01); *C12N 1/38* (2013.01)

(58) Field of Classification Search
CPC .......... C12P 7/6472; C11B 1/025; C12N 1/38
See application file for complete search history.

(56) References Cited

U.S. PATENT DOCUMENTS

| 5,928,696 A | 7/1999 | Best et al. |
|---|---|---|
| 7,732,170 B2 | 6/2010 | Bailey et al. |
| 9,848,623 B2 | 12/2017 | Bailey et al. |
| 10,531,679 B2 | 1/2020 | Rudinger et al. |
| 10,619,175 B2 | 4/2020 | Rabe et al. |
| 10,842,174 B2 | 11/2020 | Durhuus et al. |
| 11,104,923 B2 | 8/2021 | Lippmeier et al. |
| 11,261,400 B2 | 3/2022 | Bahl et al. |
| 11,324,234 B2 | 5/2022 | Silva et al. |
| 11,352,651 B2 | 6/2022 | Diehl et al. |
| 11,414,621 B2 | 8/2022 | Heining et al. |
| 11,464,244 B2 | 10/2022 | Rabe et al. |
| 11,542,220 B2 | 1/2023 | Heining et al. |
| 2009/0209014 A1 | 8/2009 | Chi et al. |
| 2012/0272566 A1 | 11/2012 | Lippmeier et al. |
| 2016/0249642 A1 | 9/2016 | Rabe et al. |
| 2017/0290356 A1 | 10/2017 | Silva et al. |
| 2017/0295823 A1 | 10/2017 | Rabe et al. |
| 2017/0295824 A1 | 10/2017 | Priefert et al. |
| 2017/0298318 A1 | 10/2017 | Rabe et al. |
| 2017/0303561 A1 | 10/2017 | Durhuus et al. |
| 2017/0306365 A1 | 10/2017 | Rabe et al. |
| 2018/0192669 A1 | 7/2018 | Wilson |
| 2019/0249108 A1 | 8/2019 | Cherinko |
| 2019/0300818 A1 | 10/2019 | Bärz et al. |
| 2019/0323043 A1 | 10/2019 | Diehl et al. |
| 2020/0231896 A1 | 7/2020 | Bahl et al. |
| 2020/0231898 A1 | 7/2020 | Bärz et al. |
| 2020/0339498 A1 | 10/2020 | Heining et al. |
| 2021/0163842 A1 | 6/2021 | Heining et al. |
| 2021/0207056 A1 | 7/2021 | Heining et al. |
| 2021/0386095 A1 | 12/2021 | Erickson et al. |
| 2022/0017929 A1 | 1/2022 | Priefert et al. |

(Continued)

FOREIGN PATENT DOCUMENTS

| WO | WO 91/07498 | 5/1991 |
|---|---|---|
| WO | WO 94/08467 | 4/1994 |
| WO | WO 97/36996 | 10/1997 |

(Continued)

OTHER PUBLICATIONS

Rodolfi et al., Biotechnology and Bioengineering, 2009, vol. 102, No. 1, p. 100-112.*
"Density" according to Wikipedia, downloaded on May 12, 2022, 10 pages of PDF.*
Wang et al., Scientific Reports, 2016, 6:30145, p. 1-9.*
Meesers et al., Appl Microbiol Biotechnol, 1996, vol. 45, p. 575-579.*
NCBI Taxonomy Browser search for genus Schizochytrium retrieved from ncbi.nlm.nih.gov/Taxonomy/Browser/wwwtax.cgiwtax.cgi, on Oct. 6, 2022, 1 page of PDF.*
Kalidasan K, Vinithkumar NV, Peter DM, Dharani G, Dufossé L. Thraustochytrids of Mangrove Habitats from Andaman Islands: Species Diversity, PUFA Profiles and Biotechnological Potential. Mar Drugs. Oct. 14, 2021;19(10):571. doi: 10.3390/md19100571. PMID: 34677470; PMCID: PMC8539084.*

(Continued)

*Primary Examiner* — Kade Ariani
(74) *Attorney, Agent, or Firm* — Law Office of Michael A. Sanzo, LLC

(57) ABSTRACT

The present invention is directed to a method of enhanced production of lipids by limitation of at least two limiting nutrient sources during the fermentation of the lipids producing cells.

17 Claims, No Drawings

(56) References Cited

U.S. PATENT DOCUMENTS

2022/0017930 A1  1/2022  Priefert et al.

FOREIGN PATENT DOCUMENTS

| | | |
|---|---|---|
| WO | WO 97/37032 | 10/1997 |
| WO | WO 01/53512 | 7/2001 |
| WO | WO 01/54510 | 8/2001 |
| WO | WO 02/10423 | 2/2002 |
| WO | WO 2011/153246 | 12/2011 |
| WO | WO 2015/095694 | 6/2015 |
| WO | WO 2015/095696 | 6/2015 |
| WO | WO 2019/063669 | 4/2019 |
| WO | WO 2019/121752 | 6/2019 |
| WO | WO 2019/122030 | 6/2019 |
| WO | WO 2019/122031 | 6/2019 |
| WO | WO 2019/191544 | 10/2019 |
| WO | WO 2019/191545 | 10/2019 |
| WO | WO 2020/036814 | 2/2020 |
| WO | WO 2020/094750 | 5/2020 |
| WO | WO 2020/094751 | 5/2020 |
| WO | WO 2020/109472 | 6/2020 |

OTHER PUBLICATIONS

Bai M, Sen B, Wen S, Ye H, He Y, Zhang X, Wang G. Culturable Diversity of Thraustochytrids from Coastal Waters of Qingdao and Their Fatty Acids. Mar Drugs. Mar. 28, 2022;20(4):229. doi: 10.3390/md20040229. PMID: 35447902; PMCID: PMC9029807.*

International Search Report for corresponding PCT/EP2018/069454, filed Jul. 18, 2018.

Written Opinion of the International Searching Authority for corresponding PCT/EP2018/069454, filed Jul. 18, 2018.

International Preliminary Report on Patentability for corresponding PCT/EP2018/069454, filed Jul. 18, 2018.

Álvarez-Díaz, et al., "Lipid Production of Microalga *Ankistrodesmus falcatus* Increased by Nutrient and Light Starvation in a Two-Stage Cultivation Process," *Appl. Biochem. Biotechnol.* 174(4):1471-1483 (Aug. 2014).

Jakobsen, et al., "Accumulation of docosahexaenoic acid-rich lipid in thraustochytrid *Aurantiochytrium* sp. strain T66: effects of N and P starvation and $O_2$ limitation," *Appl. Microbiol. Biotechnol.* 80(2):297-306 (Jun. 2008).

Praveenkumar, et al., "Influence of nutrient deprivations on lipid accumulation in a dominant indigenous microalga *Chlorella* sp., BUM11008: Evaluation for biodiesel production," *Biomass and Bioenergy* 37:60-66 (Feb. 2012).

Sun, et al., "Differential effects of nutrient limitations on biochemical constituents and docasahexaenoic acid production of *Schizochytrium* sp.," *Bioresource Technology* 159:199-206 (May 2014).

Zhu, et al., "Strategies for Lipid Production Improvement in Microalgae as a Biodiesel Feedstock,"*BioMed Research International* 2016:1-8 (Sep. 2016).

U.S. Appl. No. 15/027,429, filed Apr. 5, 2016, US-2016/0249642 A1, Sep. 1, 2016, Rabe.

U.S. Appl. No. 15/516,022, filed Mar. 31, 2017, US-2017/0295823 A1, Oct. 19, 2017, Rabe.

U.S. Appl. No. 15/516,023, filed Mar. 31, 2017, US-2017/0290356, Oct. 12, 2017, Silva.

U.S. Appl. No. 15/516,024, filed Mar. 31, 2017, US-2017/0295824 A1, Oct. 19, 2017, Priefert.

U.S. Appl. No. 15/516,038, filed Mar. 31, 2017, US-2017/0298318 A1, Oct. 19, 2017, Rabe.

U.S. Appl. No. 15/516,044, filed Mar. 31, 2017, US-2017/0306365 A1, Oct. 26, 2017, Rabe.

U.S. Appl. No. 15/516,058, filed Mar. 31, 2017, US-2017/0303561 A1, Oct. 26, 2017, Durhuus.

U.S. Appl. No. 16/317,249, filed Jan. 11, 2019, US-2019/0300818 A1, Oct. 3, 2019, Bärz.

U.S. Appl. No. 16/317,305, filed Jan. 11, 2019, NA, NA, Bärz.

U.S. Appl. No. 16/473,805, filed Jun. 26, 2019, US-2019/0323043 A1, Oct. 24, 2019, Diehl.

U.S. Appl. No. 16/644,443, filed Mar. 4, 2020, NA, NA, Bahl.

U.S. Appl. No. 15/315,094, filed Nov. 30, 2016, US-2018/0192669 A1, Jul. 12, 2018, Wilson.

U.S. Appl. No. 16/309,632, filed Dec. 13, 2018, US-2019/0249108 A1, Aug. 15, 2019, Cherinko.

U.S. Appl. No. 16/956,453, filed Jun. 19, 2021, US-2020/0339498 A1, Oct. 29, 2020, Heining.

U.S. Appl. No. 17/055,047, filed Nov. 12, 2020, US-2021/0207056 A1, Jul. 8, 2021, Heining.

U.S. Appl. No. 17/055,083, filed Nov. 12, 2020, US-2021/0163842 A1, Jun. 3, 2021, Heining.

U.S. Appl. No. 17/284,463, filed Apr. 10, 2021, US-2021/0386095 A1, Dec. 16, 2021, Erickson.

U.S. Appl. No. 17/291,608, filed May 6, 2021, US-2022/0017929 A1, Jan. 20, 2022, Priefert, et al.

U.S. Appl. No. 17/291,610, filed May 6, 2021, US-2022/0017930 A1, Jan. 20, 2022, Priefert, et al.

Jaseera, et al., "An overview of systematics, morphology, biodiversity and potential utilization of Thraustochytrids," *J. Mar. Biol. Ass. India* 62(2):13-21 (Jul.-Dec. 2020).

Leyland, et al., "Are Thraustochytrids algae?," *Fungal Biology* (2017), http://dx.doi.org/10.1016/j.funbio.2017.07.006.

* cited by examiner

ENHANCED PRODUCTION OF LIPIDS BY LIMITATION OF AT LEAST TWO LIMITING NUTRIENT SOURCES

CROSS REFERENCE TO RELATED APPLICATIONS

The present application is US national stage of international application PCT/EP2018/069454, which had an international filing date of Jul. 18, 2018, and which was published on Feb. 21, 2019. The PCT application claims the benefit of U.S. provisional application 62/546,808, filed on Aug. 17, 2017 and to European application EP 17192347.7, filed on Sep. 21, 2017. The contents of each priority application is hereby incorporated by reference in its entirety.

The present invention is directed to a method of enhanced production of lipids by limitation of at least two limiting nutrient sources during the fermentation of the lipids producing cells.

Certain eukaryotic microbes (such as algae; fungi, including yeast; and protists) have been demonstrated to be good producers of polyunsaturated fatty acids in fermenters. In particular it has been shown that high amounts of PUFAs (polyunsaturated fatty acids) can be realized, when the strains are first cultivated to a high cell density, and as a second step enhanced lipid production is initiated by reducing the amount of a limiting nutrient source like the nitrogen source or by reducing the amount of dissolved oxygen in the medium (WO 01/54510).

Starting from this state of the art, it was an object of the current invention to provide a method with even further increased yields of polyunsaturated fatty acids.

Surprisingly it has been found that better yields of PUFAs can be realized, if not only the amount of one limiting nutrient source is reduced, but if in addition the amount of a further limiting nutrient source is reduced in the course of the fermentation of the lipids producing cells, wherein those limiting nutrient sources are preferably a nitrogen source and a phosphate source.

Thus, a first subject of the current invention is a method of producing lipids containing polyunsaturated fatty acids from microorganisms, preferably eukaryotic microorganisms, capable of producing at least about 10 wt.-% of their biomass as lipids, which comprises a biomass density increasing phase and a lipid production phase, comprising
  a) adding during the biomass density increasing phase to a fermentation medium containing said microorganisms a carbon source and at least two limiting nutrient sources at a rate sufficient to increase the biomass density of said fermentation medium to at least 50 g/L, and
  b) stopping or significantly reducing the supply of at least two of said limiting nutrient sources in the lipid production phase, while supply of a carbon source is still maintained.

As used herein, the term "limiting nutrient source" refers to a source of a nutrient (including the nutrient itself) essential for the growth and cell division of a microorganism in that, when the limiting nutrient is depleted from the growth medium, its absence substantially limits the microorganism from growing or replicating further. However, since the other nutrients (and carbon source) are still in abundance, the organism can continue to make and accumulate intracellular and/or extracellular products, in particular lipids.

Such limiting nutrient sources include nitrogen sources, phosphate sources, vitamin sources (such as vitamin B2 sources, pantothenate sources, thiamine sources), trace metal sources (such as zinc sources, copper sources, cobalt sources, nickel sources, iron sources, manganese sources, molybdenum sources), and major metal sources (such as magnesium sources, calcium sources, sodium sources, potassium sources), silica sources and mixtures thereof.

Said trace metal sources and major metal sources include sulfate and chloride salts of these metals (such as $MgSO_4 * 7H_2O$; $MnCl_2 * 4H_2O$; $ZnSO_4 * 7H_2O$; $CoCl_2 * 6H_2O$; $Na_2MoO_4 * 2H_2O$; $CuSO_4 * 5H_2O$; $NiSO_4 * 6H_2O$; $FeSO_4 * 7H_2O$; $CaCl_2$; $K_2SO_4$; $KCl$; and $Na_2SO_4$) and mixtures thereof.

In a preferred embodiment of the current invention said "at least two limiting nutrient sources" are a nitrogen source and a phosphate source. In this preferred embodiment in addition to the nitrogen source(s) and the phosphate source(s), the supply of further limiting nutrient sources might be stopped or significantly reduced in the lipid production phase, as well, but preferably the other limiting nutrient sources are present in abundance in the lipid production phase.

Thus a preferred subject matter of the current invention is a method of producing lipids containing polyunsaturated fatty acids from microorganisms, preferably eukaryotic microorganisms, capable of producing at least about 10 wt.-% of their biomass as lipids, which comprises a biomass density increasing phase and a lipid production phase, comprising
  a) adding during the biomass density increasing phase to a fermentation medium containing said microorganisms a carbon source and at least two limiting nutrient sources at a rate sufficient to increase the biomass density of said fermentation medium to at least 50 g/L, and
  b) stopping or significantly reducing the supply of at least two of said limiting nutrient sources in the lipid production phase, while supply of a carbon source is still maintained, wherein said at least two limiting nutrient sources are a nitrogen source and a phosphate source.

By stopping or significantly reducing the supply of said at least two limiting nutrient sources the available amount of said limiting nutrient sources fall to concentrations, where the lipids producing microorganisms are in deprivation of said limiting nutrient sources. That means that the microorganisms could take up more of those limiting nutrient sources as are available in the medium, i.e. the supply of the limiting nutrient sources is lower than the amount of limiting nutrient sources which the microorganisms could consume. Deprivation of the first of these at least two limiting nutrient sources normally will initiate the lipid production phase, in case that initiation of the lipid production phase has not been initiated by other means before.

According to the invention, the nitrogen source may be organic, inorganic or a mixture thereof. Preferred nitrogen sources according to the invention are ammonia, urea, nitrate, nitrite, amino acids, in particular glutamate, inorganic ammonium salts, more preferably ammonium sulfate or ammonium hydroxide, and most preferably ammonium hydroxide, and mixtures thereof. The nitrogen source may also be provided in form of complex media—like peptone or yeast extract—, preferably containing components as mentioned before.

The main or only nitrogen source is more preferably selected from ammonia and inorganic ammonium salts, and is, above all, mainly or only ammonia, or mainly or only ammonium hydroxide.

According to the invention, "main nitrogen source" means that the respective source provides at least 50%, preferably at least 70%, more preferably at least 90%, of the molar nitrogen equivalents.

Preferred phosphate sources according to the invention are phosphoric acid and inorganic phosphate salts, like ammonium, calcium, sodium or potassium phosphate or corresponding hydrogen phosphate and dihydrogen phosphate salts, and mixtures thereof. The phosphate source may be provided in form of complex media, preferably containing components as mentioned before, as well.

The main or only phosphate source is preferably selected from phosphoric acid and inorganic phosphate salts, in particular potassium dihydrogen phosphate, and mixtures thereof.

Accordingly, "main phosphate source" means that the respective phosphate source provides at least 50%, preferably at least 70%, more preferably at least 90%, of molar phosphate equivalents.

Limitation of the first of these at least two limiting nutrient sources preferably initiates the lipid production phase. Thus, according to the invention, the initiation of the lipid production phase in a preferred embodiment of the invention is defined as the moment, where in the course of the fermentation the concentration of the first of those at least two limiting nutrient sources in the medium falls below 0.01 mol/l.

More generally, initiation of the lipid production phase corresponds to the moment, where further growth of the microorganisms essentially stops and the microorganisms start to strongly accumulate lipids in the cells instead. As mentioned before the lipid production phase need not necessarily be initiated by reducing the concentration of a limiting nutrient source. Alternatively it can be initiated, for example, also by limitation of the amount of dissolved oxygen in the fermentation medium.

In a preferred embodiment of the invention, the amounts of both of said two limiting nutrient sources fall to concentrations in the course of the fermentation, so that the lipids producing microorganisms in the medium are in deprivation of both of said limiting nutrient sources for at least 30% of the time of the lipid production phase, preferably for at least 40, 50 or 60% of the time of the lipid production phase, above all for at least 70, 80 or 90% of the time of the lipid production phase.

Herein, the microorganisms in the medium are preferably in deprivation of both of said limiting nutrient sources at least for the last 30% of the time of the lipid production phase, preferably at least for the last 40, 50 or 60% of the time of the lipid production phase, more preferably at least for the last 70, 80 or 90% of the time of the lipid production phase.

Alternatively, or in addition, the microorganisms in the medium are preferably in deprivation of both of said limiting nutrient sources at least for the last 30 hours of the lipid production phase, preferably at least for the last 40, 50 or 60 hours of the lipid production phase, more preferably at least for the last 70, 80 or 90 hours of the lipid production phase.

In a particularly preferred embodiment of the invention, the concentrations of both of said two limiting nutrient sources fall below 0.01 mol/l, preferably below 0.005 mol/l, in particular below 0.003 mol/l, and/or below the detection limit of those limiting nutrient sources in the course of the fermentation, respectively.

Herein, the concentrations of said both limiting nutrient sources preferably fall below 0.01 mol/l, more preferably below 0.005 mol/l, above all below 0.003 mol/l, in particular to zero and/or below the detection limit of those limiting nutrient sources, within 40 hours, preferably within 30 hours, more preferably within 20 hours, after initiation of the lipid production phase. As preferably initiation of the lipid production phase is initiated, when the concentration of the first of the at least two limiting nutrient sources falls below 0.01 mol/l, this means that the concentration of the second limiting nutrient source preferably falls below 0.01 mol/l, preferably below 0.005 mol/l, above all below 0.003 mol/l, in particular to zero and/or below the detection limit, up to 40 hours, preferably up to 30 hours, in particular up to 20 hours, later than the concentration of the first limiting nutrient source does.

Alternatively or in addition, the concentrations of said both limiting nutrient sources are below 0.01 mol/l, preferably below 0.005 mol/l, above all below 0.003 mol/l, in particular zero and/or below the detection limit of those limiting nutrient sources, at least during the complete second half of the lipid production phase, more preferably at least during the complete final 60, 70 or 80% of the time of the lipid production phase.

Alternatively or in addition, the concentrations of said both limiting nutrient sources are below 0.01 mol/l, preferably below 0.005 mol/l, above all below 0.003 mol/l, in particular zero and/or below the detection limit of those limiting nutrient sources, at least during the last 20 hours of the fermentation, more preferably at least during the last 40 hours of the fermentation, in particular at least during the last 60 hours of the fermentation.

In one embodiment of the invention during the lipid production phase no further amounts of the at least two limiting nutrient sources, in particular of nitrogen source(s) and phosphate source(s) are added, at all. Nevertheless, as depletion of those limiting nutrient sources not necessarily takes place at the same time, also in this embodiment of the invention it is possible and likely that the concentrations of both of the at least two limiting nutrient sources fall below 0.01 mol/l at different points in time. But due to the fact that supply of said limiting nutrient sources is stopped in the lipid production phase, the concentrations of said limiting nutrient sources preferably fall to zero in the course of the fermentation in this embodiment of the invention.

In a further embodiment of the current invention, the supply of one of the at least two limiting nutrient sources is stopped, before the supply of the second of the at least two limiting nutrient sources is stopped. In particular the supply of the second limiting nutrient source might be stopped up to 30 hours later, in particular up to 20 or up to 10 hours later than the supply of the first limiting nutrient source.

In a further embodiment of the current invention, supply of the limiting nutrient sources is still continued in the lipid production phase, even after reduction of their concentrations, more or less during the complete lipid production phase. In this embodiment the limiting nutrient sources are added in such small amounts that the cells will not switch back to the growth phase. This is preferably done by feeding said limiting nutrient sources in such amounts that the cells are still in deprivation of these limiting nutrient sources, preferably herein the limiting nutrient sources do not exceed a concentration of 0.01 mol/L, in particular a concentration of 0.005 mol/l, above all a concentration of 0.003 mol/l, in the lipid production phase. The benefit of this embodiment is that by still feeding those components in small amounts in the lipid production phase may help to avoid metabolic stress on the cells and by that may avoid accumulation of reactive oxygen species (ROS) inside the cells and by that hinder a possible increase of the oxidative degradation of the lipids as contained in the cells.

Addition of said limiting nutrient sources and of the carbon source may be in the form of a batch, fed-batch, continuous, bolus, and/or semi-continuous procedure. The supply of one or more of the limiting nutrient sources may also be combined with the supply of the carbon feed. "Supply" of the limiting nutrient sources and of the carbon source comprises active as well as passive supply. This means for example, that if the limiting nutrient source(s) and/or the carbon source are present in a sufficient amount in the batch medium at the beginning of the fermentation, they not necessarily have to be supplied actively in the course of the fermentation. Correspondingly, "the supply is stopped" means that the respective compound(s) is not available in the medium, anymore.

But in a preferred embodiment of the invention at least the addition of the carbon source is carried out actively in the course of the fermentation, preferably even after initiation of the lipid production phase.

In the following preferred embodiments of the invention are disclosed further, where the at least two limiting nutrient sources are a nitrogen source and a phosphate source.

In one of these preferred embodiments, the concentrations of both the nitrogen source(s) and phosphate source(s) are so low that the lipids producing microorganisms in the medium are in deprivation of both of said limiting nutrient sources for at least 30% of the time of the lipid production phase, preferably for at least 40, 50 or 60% of the time of the lipid production phase, above all for at least 70, 80 or 90% of the time of the lipid production phase.

Herein, the microorganisms in the medium are preferably in deprivation of both of said limiting nutrient sources at least for the last 30% of the time of the lipid production phase, preferably at least for the last 40, 50 or 60% of the time of the lipid production phase, more preferably at least for the last 70, 80 or 90% of the time of the lipid production phase.

Alternatively, or in addition, the microorganisms in the medium are preferably in deprivation of both of said limiting nutrient sources at least for the last 30 hours of the lipid production phase, preferably at least for the last 40, 50 or 60 hours of the lipid production phase, more preferably at least for the last 70, 80 or 90 hours of the lipid production phase.

In a further of these preferred embodiments, the amount of the nitrogen source(s) is reduced below a concentration of $5.6 \times 10^{-3}$ mol/l (corresponding in case of ammonium as nitrogen source to 0.1 g/l ammonium) and the amount of the phosphate source(s) is reduced below a concentration of $5.4 \times 10^{-3}$ mol/l (corresponding to 0.5 g/l phosphate) in the course of the fermentation, preferably within a time window of not more than 40 hours, more preferably not more than 30 hours, in particular not more than 20 or 10 hours.

Herein, the amount of the nitrogen source(s) is preferably reduced below a concentration of $2.8 \times 10^{-3}$ mol/l (corresponding in case of ammonium as nitrogen source to 0.05 g/l ammonium) and the amount of the phosphate source(s) is preferably reduced below a concentration of $5.4 \times 10^{-4}$ mol/l (corresponding to 0.05 g/l phosphate), preferably within a time window of not more than 40 hours, more preferably not more than 30 hours, in particular not more than 20 or 10 hours.

Herein the lipid production phase is preferably initiated by either first limiting the amount of the nitrogen source(s) or by first limiting the amount of the phosphate source(s) or by (more or less) simultaneously limiting the amount of the nitrogen source(s) and the phosphate source(s).

The molar concentrations as mentioned in the description relate to monovalent nitrogen and phosphate source(s). It is evident that in case that a multivalent nitrogen or phosphate source is used as alternative or in addition to a monovalent nitrogen or phosphate source, then only a corresponding fraction of the mentioned molar concentration has to be applied. For example, in case of a bivalent source only half of the molar concentration has to be applied etc. Further it is also evident that in case that complex media containing such nitrogen or phosphate sources are used as alternative or in addition to a monovalent nitrogen or phosphate source, that then the amount of nitrogen or phosphate source as contained in the complex media is relevant for the calculation.

In a particular embodiment of the invention, the amount of both the nitrogen source(s) and the phosphate source(s) is reduced to zero and/or below the detection limit of those compounds within a time window of not more than 40 hours, preferably not more than 30 hour, more preferably not more than 20 or 10 hours.

Determination of the amount of ammonia/ammonium is preferably carried out in a sample of the reaction medium by UV spectroscopy as follows: Ammonia/ammonium is reacted in presence of a glutamate dehydrogenase, 2-oxo-glutarate and NADH to L-glutamate, NAD+ and water. As the amount of oxidized NADH is stoichiometric to the amount of ammonia/ammonium as present in the sample, by comparing the amount of NADH before and after the reaction, the amount of ammonia/ammonium can be determined. The amount of NADH can be determined by means of light absorbance at 334, 340 or 365 nm. A suitable commercially available kit for determining the amount of ammonia/ammonium is the r-Biopharm Ammonium test kit (Roche Diagnostics, Switzerland).

Determination of the amount of phosphate is preferably carried out in a sample of the reaction medium by colorimetry as follows: Phosphate is reacted with ammonium molybdate to form ammonium phosphomolybdate. The ammonium phosphomolybdate is then further reduced by a reducing agent to produce a stable, reduced, mixed-valance heteropolymolybdate complex $PO_4[M(V)O_3)_4(Mo(VI)O_3)_8]^{7-}$. The rate of change of absorbance of the resulting blue heteropolymolybdate complex is proportional to the phosphate concentration as originally contained in the sample. The colorimetric determination of the amount of phosphate can be carried out by using a BioProfile Chemistry Analyzer 300 (Nova Biomedical, Waltham, USA).

In a preferred embodiment of the invention, the concentration of the nitrogen source(s) is always below $5.6 \times 10^{-3}$ mol/l (corresponding in case of ammonium as nitrogen source to 0.1 g/l ammonium) and the concentration of the phosphate source(s) is always below $5.4 \times 10^{-3}$ mol/l (corresponding to 0.5 g/l phosphate) at least during the last 50 or 70%, preferably at least during the last 80%, more preferably at least during the last 90%, of the period of the lipid production phase.

Herein in a special embodiment of the invention, the concentration of the nitrogen source(s) is always below $5.6 \times 10^{-3}$ mol/l and the concentration of the phosphate source(s) is always below $5.4 \times 10^{-3}$ mol/l during the complete lipid production phase.

In a very preferred embodiment of the invention, the concentration of the nitrogen source(s) is always below $2.8 \times 10^{-3}$ mol/l (corresponding in case of ammonium as nitrogen source to 0.05 g/l ammonium) and the concentration of the phosphate source(s) is always below $5.4 \times 10^{-4}$ mol/l (corresponding to 0.05 g/l phosphate) at least during the last 50 or 70%, preferably at least during the last 80%, more preferably at least during the last 90%, of the period of the lipid production phase.

Herein, in a special embodiment of the invention, the concentration of the nitrogen source(s) is always below $2.8 \times 10^{-3}$ mol/l and the concentration of the phosphate source(s) is always below $5.4 \times 10^{-4}$ mol/l during the complete lipid production phase.

In a further preferred embodiment of the invention, the concentration of the nitrogen source(s) and the phosphate source(s) is zero and/or always below the detection limit at least during the last 50 or 70%, preferably at least during the last 80%, more preferably at least during the last 90%, of the period of the lipid production phase.

Herein, in a special embodiment of the invention, the concentration of the nitrogen source(s) and the phosphate source(s) is always zero and/or below the detection limit of such compounds, in particular by using the methods as mentioned before, during the complete lipid production phase.

As in a very preferred embodiment of the invention, no nitrogen source(s) and no phosphate source(s) are added after the nitrogen source(s) and the phosphate source(s) have been consumed by the microorganisms, it has to be assumed that the concentration of the nitrogen source(s) and the phosphate source(s) is indeed zero or at least almost zero in this very preferred embodiment during the complete lipid production phase or at least during the last 70, 80 or 90% of the time period of the lipid production phase.

A preferred time period of the lipid production phase is from 50 to 150 hours, more preferably from 70 to 130 hours, in particular from 90 to 110 hours.

The microorganisms which produce a PUFAs containing lipid are described extensively in the prior art. Preferably they are eukaryotic microorganisms. The cells used may, in this context, in particular be cells which already naturally produce PUFAs; however, they may also be cells which, as the result of suitable genetic engineering methods or due to random mutagenesis, show an improved production of PUFAs or have been made capable of producing PUFAs, at all. The production of the PUFAs may be autotrophic, mixotrophic or heterotrophic. Preferably, the microorganisms are capable of producing the PUFAs due to a polyketide synthase like system. The polyketide synthase like system may be an endogenous one or, due to genetic engineering, an exogenous one.

The biomass preferably comprises cells which produce PUFAs heterotrophically. The cells according to the invention are preferably selected from algae, fungi, particularly yeasts, bacteria, plant cells, or protists. Suitable cells of oil-producing yeasts are, in particular, strains of *Yarrowia, Candida, Rhodotorula, Rhodosporidium, Cryptococcus, Trichosporon* and *Lipomyces*. The cells are more preferably microbial algae, microalgae, or fungi.

Suitable cells of oil-producing microalgae and algae-like microorganisms are, in particular, microorganisms selected from the phylum Stramenopiles (also called Heterokonta). The microorganisms of the phylum Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales. Other preferred groups of microalgae include the members of the green algae and dinoflagellates, including members of the genus *Crypthecodinium*.

The biomass according to the invention preferably comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae (also called Thraustochytrids) includes the genera *Althornia, Aplanochytrium, Aurantiochytrium, Botryochytrium, Elnia, Japonochytrium, Oblongichytrium, Parietichytrium, Schizochytrium, Sicyoidochytrium, Thraustochytrium,* and *Ulkenia*. The biomass particularly preferably comprises cells from the genera *Aurantiochytrium, Oblongichytrium, Schizochytrium,* or *Thraustochytrium*, above all from the genus *Schizochytrium*.

In accordance with the invention, the polyunsaturated fatty acid (PUFA) is preferably a highly-unsaturated fatty acid (HUFA), in particular a highly-unsaturated long chain fatty acid (lcHUFA).

The cells present in the biomass are preferably distinguished by the fact that they contain at least 20% by weight, preferably at least 30% by weight, in particular at least 35% by weight, more preferably at least 40% by weight, of PUFAs, in each case based on cell dry matter.

According to the current invention, the term "lipid" includes phospholipids; free fatty acids; esters of fatty acids; triacylglycerols; diacylglycerols; monoacylglycerols; sterols and sterol esters; carotenoids; xanthophylls (e. g., oxycarotenoids); hydrocarbons; isoprenoid-derived compounds and other lipids known to one of ordinary skill in the art. The terms "lipid" and "oil" are used interchangeably according to the invention.

In a preferred embodiment of the invention, the majority of the lipids is present in the form of triacylglycerols, with preferably at least 50% by weight, in particular at least 75% by weight and, in an especially preferred embodiment, at least 90% by weight of the lipids present in the cell being present in the form of triglycerides.

According to the invention, polyunsaturated fatty acids (PUFAs) are understood to mean fatty acids having at least two, particularly at least three, C—C double bonds. According to the invention, highly-unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerols. In a preferred embodiment, the majority of the PUFAs is present in the form of triacylglycerols, with preferably at least 50% by weight, in particular at least 75% by weight and, in an especially preferred embodiment, at least 90% by weight of the PUFAs present in the cell being present in the form of triacylglycerols.

Preferably the lipids as contained in the cells comprise PUFAs in an amount greater than 15 wt.-%, preferably greater than 20, 25 or 30 wt.-%, more preferably greater than 35 or 40 wt.-%, still more preferably greater than 45 or 50 wt.-%, and most preferably greater than 55 wt.-% Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z, 16Z,19Z)-docosa-4,7,10,13,16,19-hexaenoic acid.

In a very preferred embodiment of the current invention, cells, in particular a *Schizochytrium* strain, is employed which produces a significant amount of EPA and DHA, simultaneously, wherein DHA is preferably produced in an amount of at least 20 wt.-%, preferably in an amount of at least 30 wt.-%, in particular in an amount of 30 to 50 wt.-%, and EPA is produced in an amount of at least 5 wt.-%, preferably in an amount of at least 10 wt.-%, in particular in an amount of 10 to 20 wt.-% (in relation to the total amount of lipid as contained in the cells, respectively). DHA and EPA producing *Schizochytrium* strains can be obtained by consecutive mutagenesis followed by suitable selection of mutant strains which demonstrate superior EPA and DHA production and a specific EPA:DHA ratio under specific cultivation conditions. Any chemical or nonchemical (e.g. ultraviolet (UV) radiation) agent capable of inducing genetic change to the microbial cell can be used as the mutagen. These agents can be used alone or in combination with one another, and the chemical agents can be used neat or with a solvent. Those methods are well known to those skilled in the art.

Preferred species of microorganisms of the genus *Schizochytrium*, which produce EPA and DHA simultaneously, are deposited under ATCC Accession No. PTA-9695, PTA-9696, PTA-9697, PTA-9698, PTA-10208, PTA-10209, PTA-10210, or PTA-10211. PTA-10212, PTA-10213, PTA-10214, PTA-10215.

Methods for producing the biomass, in particular a biomass which comprises cells containing lipids, in particular PUFAs, particularly of the order Thraustochytriales, are described in detail in the prior art (see e.g. WO91/07498, WO94/08467, WO97/37032, WO97/36996, WO01/54510). As a rule, the production takes place by cells being cultured in a fermenter in the presence of a carbon source and of a nitrogen source, along with a number of additional substances like minerals that allow growth of the microorganisms and production of the PUFAs. In this context, biomass densities of more than 100 grams per liter and production rates of more than 0.5 gram of lipid per liter per hour may be attained. The method is preferably carried out in what is known as a fed-batch method, i.e. the carbon and further nutrient sources are fed in incrementally during the fermentation. When the desired biomass has been obtained, lipid production is induced as described before.

In a preferred embodiment of the current invention, the cells are grown in the biomass density increasing phase until they reach a biomass density of at least 80 or 100 g/l, more preferably at least 120 or 140 g/l, in particular at least 160 or 180 g/l, above all at least 200 g/l (calculated as dry-matter content). Such processes are for example disclosed in U.S. Pat. No. 7,732,170.

Determination of the biomass density can be carried out by gravimetric analysis: For doing that, a sample of the fermentation broth with a specific volume is weighed before and after freeze-drying. The remaining weight of the dried sample corresponds to the biomass as contained in that specific volume of fermentation broth.

Preferably, the cells are fermented in a medium with low salinity, in particular so as to avoid corrosion. This can be achieved by using chlorine-free sodium salts as the sodium source instead of sodium chloride, such as, for example, sodium sulfate, sodium carbonate, sodium hydrogen carbonate or soda ash (a mixture of sodium carbonate and sodium oxide). Preferably, chloride is used in the fermentation in amounts of less than 3 g/l, in particular less than 500 mg/l, especially preferably less than 100 mg/l.

The sodium concentration is (expressed as g/L of Na) preferably at least about 1 g/L, more preferably in the range of from 1 g/L to 50 g/L and more preferably in the range of from 2 g/L to 25 g/L.

Suitable carbon sources are both alcoholic and non-alcoholic carbon sources. Examples of alcoholic carbon sources are methanol, ethanol, isopropanol, and glycerol. Examples of non-alcoholic carbon sources are fructose, glucose, sucrose, molasses, starch, in particular corn starch, corn syrup, cane sugar and beet sugar. Fatty acids, in the form of hydroxy fatty acids, triacylglycerides, and di- and monoacylglycerides can also serve as the carbon source. An appropriate range of the amount of carbon source needed for a particular microorganism during a fermentation process is well known to one of ordinary skill in the art.

The cells are preferably fermented at a pH of 3 to 11, in particular 4 to 10, and preferably at a temperature of at least 15° C., in particular 20 to 40° C., more preferably at least 24° C., in particular at least 28° C. A typical fermentation process takes up to approximately 200 hours. A typical lipid production phase of such a fermentation process takes up to about 100 hours.

Processes of the present invention preferably provide an average lipid production rate of at least about 0.3 g/L/hr, more preferably at least about 0.4 g/L/hr, in particular at least about 0.5 g/L/hr, and most preferably at least about 0.6 g/L/hr.

Preferably, processes of the present invention provide an average PUFA production rate of at least about 0.2 g of PUFAs/L/hr, in particular at least about 0.3 g of PUFAs/L/hr, more preferably at least about 0.4 g of PUFAs/L/hr, and most preferably at least about 0.5 g of PUFAs/L/hr, wherein PUFAs refers preferably to a mixture of DHA and EPA.

In a preferred embodiment of the current invention, the microorganisms are grown in a fed-batch process. A fed-batch process is a fermentation process, where one or more substrates are added in increments.

Processes of the present invention for growing microorganisms include a biomass density increasing phase. In the biomass density increasing phase, the primary objective of the fermentation process is to increase the biomass density in the fermentation medium to obtain the biomass densities described above. The rate of carbon source supply is typically maintained at a particular level or range that does not cause a significant detrimental effect on biomass productivity of microorganisms, or the viability of the microorganisms resulting from insufficient capabilities of the fermentation equipment to remove heat from and transfer gases to and from the liquid broth The biomass density increasing phase takes place in a typical technical fermentation in different phases, for example the fermentation may comprise a pre-seed stage or a number of pre-seed stages, and a seed stage which is finally transferred to the production stage fermentation.

In a preferred embodiment of the invention all limiting nutrient sources, in particular the limiting nitrogen and phosphate sources are continuously present in high abundance before initiation of the lipid production phase to allow maximal growth of the biomass. This means in particular that the presence of the limiting nitrogen and phosphate sources is still detectable in the fermentation broth by applying for measuring the methods as mentioned before, when the pre-seed or seed stage has finished and the resulting fermentation broth has further been transferred to the next fermentation stage. However, the concentrations must also not be too high to avoid detrimental effects on the microorganisms. Preferably, before initiation of the lipid production phase, the concentration of the limiting nitrogen source(s) is always well above $5.6 \times 10^{-3}$ mol/l (corresponding to 0.1 g/l ammonium) and the concentration of the limiting phosphate source(s) is always well above $5.4 \times 10^{-3}$ mol/l (corresponding to 0.5 g/l phosphate).

Processes of the present invention for growing microorganisms also include a lipid production phase. In this phase, the primary use of the substrate by the microorganisms is not increasing the biomass density but rather using the substrate to produce lipids. It should be appreciated that lipids are also produced by the microorganisms in smaller amounts during the biomass density increasing phase; however, as stated above, the primary goal in the biomass density increasing phase is to increase the biomass density.

The dissolved oxygen level (DO) in the fermentation medium during the biomass density increasing phase is preferably at least about 8% of saturation, and preferably between 10% and 20% of saturation, during the production phase the dissolved oxygen in the fermentation medium is normally kept in the same range like in the biomass density increasing phase, but might also be reduced to about 3% of saturation or less. At the beginning of the fermentation the DO can be at or near saturation and as the microbes grow it may allowed to drift down to these low DO set-points. In one particular embodiment of the present invention, the amount of dissolved oxygen level in the fermentation medium is varied during the fermentation process.

The amount of dissolved oxygen present in the fermentation medium can be controlled by controlling the amount of oxygen in the head-space of the fermenter by increasing or decreasing the aeration rate, by controlling the speed at which the fermentation medium is agitated (or stirred), or by controlling the back-pressure in the medium, or by a combination of such parameters. For example, a high agitation (or stirring) rate and/or a high aeration rate results in a relatively higher amount of dissolved oxygen in the fermentation medium than a low agitation rate and/or low aeration rate.

After the fermentation has ended, the cells may be pasteurized in order to kill the cells and to deactivate enzymes which might promote lipid degradation. The pasteurization is preferably effected by heating the biomass to a temperature of 50 to 121° C., preferably 50 to 70° C., for a period of 5 to 80 minutes, in particular 20 to 60 minutes.

Likewise, after the fermentation is ended, antioxidants may be added in order to protect the PUFAs present in the biomass from oxidative degradation. Preferred antioxidants in this context are BHT, BHA, TBHA, gallate, propyl-galate, ethoxyquin, beta-carotene, vitamin E and vitamin C. The antioxidant, if used, is preferably added in an amount of 0.01 to 2% by weight.

Any currently known isolation methods can be used to isolate microorganisms from the fermentation medium, including centrifugation, filtration, ultrafiltration, decantation, and solvent evaporation.

In a preferred embodiment of the invention, after the fermentation of the eukaryotic microorganisms, a lipid recovery process is following. Lipid recovering may for example comprise removing water from said fermentation medium to provide dry microorganisms; and subsequently isolating said lipids from said dry microorganisms. The water removal step may comprise drying the fermentation broth either directly or after concentration of the fermentation broth on a drum-dryer or on a fluidized bed granulator without prior centrifugation.

The lipid recovery process may alternatively also comprise treating the fermentation broth to permeabilize, lyse or rupture the microbial cells and subsequently recovering the lipids from the fermentation broth by gravity separation, and preferably centrifugation, with or without the aid of a water-soluble solvent to aid in breaking the lipid/water emulsion. Processes for lysing the cells in the fermentation broth are for example described in WO 2001/053512, WO 2002/010423, WO 2011/153246, WO 2015/095694 and WO 2015/095696. Preferred processes for recovering the lipids once the cells are permeabilized, broken or lysed in the fermentation broth (which enables the lipid emulsion to be broken, and the lipid-rich fraction to be recovered) include the de-oiling process outlined in WO 96/05278. In this process a water soluble compound, e. g., alcohol or acetone, is added to the oil/water emulsion to break the emulsion and the resulting mixture is separated by gravity separation, e. g., centrifugation. This process can also be modified to use other agents (water and/or lipid soluble) to break the emulsion.

Microorganisms, lipids extracted therefrom, the biomass remaining after lipid extraction or combinations thereof can be used directly as a food ingredient, such as an ingredient in beverages, sauces, dairy based foods (such as milk, yogurt, cheese and ice-cream) and baked goods; nutritional supplement (in capsule or tablet forms); feed or feed supplement for any animal whose meat or products are consumed by humans; food supplement, including baby food and infant formula; and pharmaceuticals (in direct or adjunct therapy application). The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs, milk or other products. When fed to such animals, polyunsaturated lipids can be incorporated into the flesh, milk, eggs or other products of such animals to increase their content of these lipids.

EXAMPLES

Example 1: Production of Lipid Containing Biomass of *Schizochytrium* Sp ATCC PTA-9695 by Single Limitation of Ammonia at Transition into the Lipid Production Phase of the Main Fermentation Cultures were inoculated with 10% (wt/wt) of a seed fermentation of ATCC PTA-9695 and cells were cultivated in total for about 192 hours in 10 L fermenters with a start mass of 7.5 liters and a final mass of 10 liters. During the fermentation a dextrose solution of 85% (wt/vol) was fed to maintain a glucose concentration of about 50 g/l in the fermentation broth. In the biomass formation phase (about 60 hours of the fermentation time) the ammonia concentration in the broth was maintained in a range between 0.2 and 0.4 g/l. At certain intervals $KH_2PO_4$ solution was added to keep the phosphate concentration between 0.5 and 2 g/l during the whole time of the fermentation. The pH setpoint was maintained by titration with ammonia water into the fermenter. After about 60 hours of fermentation it was decided to initiate the transition into the oil production phase by stopping the titration of ammonia water, leading to complete exhaustion of the ammonia from the broth, and instead switching to titration with NaOH, while $KH_2PO_4$ titration was maintained. Particularly, the phosphate was kept during the oil production phase at a concentration of about 0.5 g/l in one run and at a concentration of about 1.5 g/l in another run. The dissolved oxygen (DO) level was maintained at 20% saturation or higher in the broth during the whole fermentation. The DO was controlled by stirrer speed.

The start medium of the main-fermenter had the following composition:

| Compound | Formula | Concentration | | Optional ranges |
|---|---|---|---|---|
| Sodium sulfate | $NaSO_4$ | g/L | 8.8 | 0-25, 2-20, or 3-10 |
| Sodium chloride | NaCl | g/L | 0.625 | 0-25, 0.1-10, or 0.5-5 |
| Potassium chloride | KCl | g/L | 1 | 0-5, 0.25-3, or 0.5-2 |
| Magnesium sulfate | $MgSO_4 * 7H_2O$ | g/L | 5 | 0-10, 2-8, or 3-6 |
| Ammonium sulfate | $(NH_4+)_2SO_4$ | g/L | 0.42 | 0-10, 0.25-5, or 0.05-3 |
| Calcium chloride | $CaCl_2 * 2H_2O$ | g/L | 0.29 | 0.1-5, 0.15-3, or 0.2-1 |
| Yeast Extract | | g/L | 1 | 0-20, 0.1-10, or 0.5-5 |
| Mono-potassium phosphate | $KH_2PO_4$ | g/L | 1.765 | 0.1-10, 0.5-5, or 1-3 |
| Post autoclave (Metals) | | | | |
| Citric acid | $C_6H_8O_7 * H_2O$ | mg/L | 46.82 | 0.1-5000, 10-3000, or 40-2500 |
| Ferrous (II)+ sulfate | $FeSO_4 * 7H_2O$ | mg/L | 10.3 | 0.1-100, 1-50, or 5-25 |
| Manganese chloride | $MnCl_2 * 4H_2O$ | mg/L | 3.1 | 0.1-100, 1-50, or 2-25 |
| Zinc sulfate | $ZnSO_4 * 7H_2O$ | mg/L | 9.3 | 0.01-100, 1-50, or 2-25 |
| Sodium molybdate | $Na_2MoO_4 * 2H_2O$ | mg/L | 0.04 | 0-1, 0.001-0.1, or 0.01-0.1 |
| Copper sulfate | $CuSO_4 * 5H_2O$ | mg/L | 2.07 | 00.1-100, 0.5-50, or 1-25 |
| Nickel sulfate | $NiSO_4 * 6H_2O$ | mg/L | 2.07 | 0.1-100, 0.5-50, or 1-25 |
| Post Autoclave (Vitamins) | | | | |
| Thiamin* HCL | $C_{12}H_{18}Cl_2N_4OS$ | mg/L | 9.75 | 0.1-100, 1-50, or 5-25 |
| Calcium D(+)-pantothenate | $C_{18}H_{32}Ca_{14}N_2O_{10}$ | mg/L | 3.33 | 0.1-100, 0.1-50, or 1-10 |
| Biotin 1% D(+) | $C_{10}H_{16}N_2O_3S$ | mg/L | 0.00358 | 0.1-100, 0.1-50, or 1-10 |
| Post autoclave (Carbon) | | | | |
| Dextrose | $C_6H_{12}O_6$ | g/L | 30 | 5-150, 10-100, or 20-50 |

| Nitrogen Feed | Target Nitrogen Feed Addition | Optional ranges |
|---|---|---|
| NH4OH (28-30% w/w) | 23.6 mL/L | 0-150, 10-100, or 15-50 |

Cultivation conditions were as follows:

| Parameter | Value | Optional ranges | Remark |
|---|---|---|---|
| Temperature | 22.5° C. | 18-30; 20-27; 22-25 | |
| Dissolved Oxygen (DO) | ≥20% | 10-100; 15-75; 20-60 | |
| pH | 7.0 | 6.5-7.5; 6.7-7.3; 6.8-7 | Controlled by addition of ammonia water or NaOH |

After a fermentation time of 192 h in total, the fermentation process was stopped by heating the broth to 60° C. for 20 minutes, which stopped the metabolism of the cells. Subsequently, the total amount of oil as produced by the cells was determined. It turned out that stopping the nitrogen supply, while simultaneously maintaining the phosphate supply at concentrations of about 500 mg/l or about 1500 m/l lead to final total fat content in the cells of 47 and 43%, respectively.

Example 2: Production of Lipid Containing Biomass of *Schizochytrium* Sp ATCC PTA-9695 by Single Limitation of PO4 at Transition into the Lipid Production Phase of the Main Fermentation Cultures were inoculated with 10% (wt/wt) of seed fermentation of ATCC PTA 9695 and cells were cultivated in total for about 192 hours in fermenters with a start mass of 7.5 liters and a final mass of 10 liters. During the fermentation a dextrose solution of 85% (wt/vol) was fed to maintain a glucose concentration of about 50 g/l in the fermentation broth. In the biomass formation phase (about 60 hours of the fermentation time) phosphate concentration in the broth was maintained between 500 and 2000 mg/l by adding $KH_2PO_4$ solution at certain intervals. To initiate the oil production phase, the PO4 concentration was allowed to continuously drop until it was completely exhausted from the broth. The ammonia concentration was maintained during the whole fermentation, and in particular during the oil production phase, in range between 0.2-0.4 g/l. The pH setpoint was maintained by titration with ammonia water into the fermenter or by titration of a combination of ammonia water and NaOH. The dissolved oxygen (DO) level was maintained at 20% saturation or higher in the broth during the whole fermentation. The DO was controlled by stirrer speed.

The start medium of the main-fermenter had the following composition:

| Compound | Formula | Concentration | | Ranges |
|---|---|---|---|---|
| Sodium sulfate | $NaSO_4$ | g/L | 8.8 | 0-25, 2-20, or 3-10 |
| Sodium chloride | NaCl | g/L | 0.625 | 0-25, 0.1-10, or 0.5-5 |
| Potassium chloride | KCl | g/L | 1 | 0-5, 0.25-3, or 0.5-2 |
| Magnesium sulfate | $MgSO_4 * 7H_2O$ | g/L | 5 | 0-10, 2-8, or 3-6 |

-continued

| Compound | Formula | Concentration | | Ranges |
|---|---|---|---|---|
| Ammonium sulfate | $(NH_4+)_2SO_4$ * | g/L | 0.42 | 0-10, 0.25-5, or 0.05-3 |
| Calcium chloride | $CaCl_2$ * $2H_2O$ | g/L | 0.29 | 0.1-5, 0.15-3, or 0.2-1 |
| Yeast Extract | | g/L | 1 | 0-20, 0.1-10, or 0.5-5 |
| Mono-potassium phosphate | $KH_2PO_4$ | g/L | 1.765 | 0.1-10, 0.5-5, or 1-3 |

Post autoclave (Metals)

| Compound | Formula | Concentration | | Ranges |
|---|---|---|---|---|
| Citric acid | $C_6H_8O_7$ * $H_2O$ | mg/L | 46.82 | 0.1-5000, 10-3000, or 40-2500 |
| Ferrous (II)+ sulfate | $FeSO_4$ * $7H_2O$ | mg/L | 10.3 | 0.1-100, 1-50, or 5-25 |
| Manganese chloride | $MnCl_2$ * $4H_2O$ | mg/L | 3.1 | 0.1-100, 1-50, or 2-25 |
| Zink sulfate | $ZnSO_4$ * $7H_2O$ | mg/L | 9.3 | 0.01-100, 1-50, or 2-25 |
| Sodium molybdate | $Na_2MoO_4$ * $2H_2O$ | mg/L | 0.04 | 0-1, 0.001-0.1, or 0.01-0.1 |
| Copper sulfate | $CuSO_4$ * $5H_2O$ | mg/L | 2.07 | 00.1-100, 0.5-50, or 1-25 |
| Nickel sulfate | $NiSO_4$ * $6H_2O$ | mg/L | 2.07 | 0.1-100, 0.5-50, or 1-25 |

Post Autoclave (Vitamins)

| Compound | Formula | Concentration | | Ranges |
|---|---|---|---|---|
| Thiamin* HCL | $C_{12}H_{18}Cl_2N_4OS$ | mg/L | 9.75 | 0.1-100, 1-50, or 5-25 |
| Calcium D(+)-pantothenate | $C_{18}H_{32}Ca_{14}N_2O_{10}$ | mg/L | 3.33 | 0.1-100, 0.1-50, or 1-10 |
| Biotin 1% D(+) | $C_{10}H_{16}N_2O_3S$ | mg/L | 0.00358 | 0.1-100, 0.1-50, or 1-10 |

Post autoclave (Carbon)

| Compound | Formula | Concentration | | Ranges |
|---|---|---|---|---|
| Dextrose | $C_6H_{12}O_6$ | g/L | 30 | 5-150, 10-100, or 20-50 |

| Phosphate Feed | Target Phosphate Feed Addition | Range |
|---|---|---|
| $KH_2PO_4$ Solution (8.75% w/w) | 40 mL/L | 5-150, 15-100, or 20-75 |

Cultivation conditions were as follows:

| Parameter | Value | Optional ranges | Remark |
|---|---|---|---|
| Temperature | 22.5° C. | 18-30; 20-27; 22-25 | |
| Dissolved Oxygen (DO) | ≥20% | 10-100; 15-75; 20-60 | |
| pH | 7.0 | 6.5-7.5; 6.7-7.3; 6.8-7 | Controlled by addition of ammonia water and/or NaOH |

After a fermentation time of 192 h in total, the fermentation process was stopped by heating the broth to 60° C. for 20 minutes, which stopped the metabolism of the cells. Subsequently, the total amount of oil as produced by the cells was determined. It turned out that stopping the phosphate supply, while simultaneously maintaining the ammonia supply at concentrations between 0.2 and 0.4 g/l lead to a final total fat content in the cells of between 50 and 60%.

Example 3: Production of Lipid Containing Biomass of *Schizochytrium* Sp. ATCC PTA-9695 by Simultaneous Limitation of Ammonia and Phosphate at Transition into the Lipid Production Phase of the Main Fermentation This fermentation was run essentially under the same conditions as described in "Example 1" with $KH_2PO_4$ solution added only in the biomass formation phase of the fermentation to keep the phosphate concentration between 500 and 2000 mg/l. After the biomass formation phase the phosphate concentration was allowed to continuously drop without further addition of $KH_2PO_4$ solution. By removing addition of the $KH_2PO_4$ solution, the culture run into simultaneous limitation of ammonia and phosphate. It turned out that stopping both the phosphate supply and the ammonia supply, delivered the best yield of final total fat in the cells, namely an amount of total fat of about 70%.

The invention claimed is:

1. A method of producing lipids comprising polyunsaturated fatty acids by the fermentation of a microorganism of the genus *Schizochytrium* or the genus *Aurantiochytrium*, said fermentation comprising:
   a) a biomass concentration increasing phase, in which a carbon source and at least two limiting nutrient sources are added to fermentation medium containing said microorganism to increase the biomass concentration of said fermentation medium to at least 50 g/L; and
   b) a lipid production phase in which the addition of at least two of said limiting nutrient sources is stopped or reduced while supply of the carbon source is maintained;
   wherein one of the two limiting nutrient sources is a source of phosphate and the other is a source of nitrogen.

2. The method of claim 1, wherein by stopping or reducing the addition of at least the two limiting nutrient sources, the amounts of said limiting nutrient sources fall to concentrations where the microorganism is in deprivation of said limiting nutrient sources.

3. The method of claim 2, wherein the microorganism is in deprivation of both of said at least two limiting nutrient sources for at least 30% of the time of the lipid production phase.

4. The method of claim 1, wherein the concentration of both of said at least two limiting nutrient sources falls below 0.01 mol/l in the course of the fermentation.

5. The method of claim 4, wherein the concentrations of said at least two limiting nutrient sources fall below 0.01 mol/l within 40 hours after initiation of the lipid production phase.

6. The method of claim 1, wherein the concentrations of said at least two limiting nutrient sources are below 0.01 mol/l, at least during the final 40% of the time of the lipid production phase.

7. The method of claim 1, wherein the concentrations of said at least two limiting nutrient sources are below 0.01 mol/l, at least during the last 20 hours of the fermentation.

8. The method of claim 1, wherein the nitrogen source is selected from the group consisting of: ammonia, urea, a nitrate, a nitrite, an amino acid, an inorganic ammonium salt, and mixtures thereof.

9. The method of claim 8, wherein the phosphate source is selected from the group consisting of: phosphoric acid; an inorganic phosphate salt, a hydrogen phosphate salt; a dihydrogen phosphate salt, and mixtures thereof.

10. The method of claim 9, wherein said nitrogen source comprises an inorganic ammonium salt, ammonia, or mixtures thereof.

11. The method of claim 9, wherein the phosphate source comprises phosphoric acid, inorganic phosphate salts, or mixtures thereof.

12. The method of claim 9, wherein, in the lipid production phase, the nitrogen source is reduced to below a concentration of $5.6 \times 10^{-3}$ mol/l and the phosphate source is reduced to below a concentration of $5.4 \times 10^{-3}$ mol/l within a time window of not more than 40 hours.

13. The method of claim 9, wherein, in the lipid production phase, the amount of the nitrogen source and the phosphate source is reduced to zero and/or below the detection limit of those compounds within a time window of not more than 40 hours.

14. The method of claim 9, wherein the concentration of the nitrogen source is always below $5.6 \times 10^{-3}$ mol/l and the concentration of the phosphate source(s) is always below $5.4 \times 10^{-3}$ mol/l during at least the last 75% of the time of the lipid production phase.

15. The method of claim 1, wherein, during the lipid production phase, the supply of the at least two limiting nutrient sources is stopped.

16. The method of claim 1, wherein the biomass concentration increasing phase is carried out until a biomass concentration of at least 80 g/L is reached.

17. A method of producing lipids comprising polyunsaturated fatty acids by the fermentation of a microorganism of the genus *Schizochytrium* or *Aurantiochytrium*, said fermentation comprising:
a) a biomass concentration increasing phase, in which a carbon source and at least two limiting nutrient sources are added to fermentation medium containing said microorganism to increase the biomass concentration of said fermentation medium to at least 50 g/L; and
b) a lipid production phase in which the addition of at least two of said limiting nutrient sources is stopped or reduced while supply of the carbon source is maintained;
wherein:
one of the two limiting nutrient sources is a source of phosphate is selected from the group consisting of: phosphoric acid; an inorganic phosphate salt, a hydrogen phosphate salt; a dihydrogen phosphate salt, and mixtures thereof;
the other is a source of nitrogen selected from the group consisting of: ammonia, urea, a nitrate, a nitrite, an amino acid, an inorganic ammonium salt, and mixtures thereof; and
the carbon source is selected from the group consisting of: methanol, ethanol, isopropanol, glycerol, fructose, glucose, sucrose, molasses, starch, cane sugar; beet sugar, hydroxy fatty acids, triacylglycerides, diglycerides, monoacylglycerides and mixtures thereof.

* * * * *